United States Patent
Radhakrishnan et al.

(10) Patent No.: US 6,926,906 B2
(45) Date of Patent: Aug. 9, 2005

(54) ORALLY ADMINISTRABLE PHARMACEUTICAL FORMULATION

(75) Inventors: Ramachandran Radhakrishnan, Bangalore (IN); Nehru Babu Gaddipati, Somerset, NJ (US)

(73) Assignee: M./S. Strides, Inc., Somerset, NJ (US)

( * ) Notice: Subject to any disclaimer, the term of this patent is extended or adjusted under 35 U.S.C. 154(b) by 0 days.

(21) Appl. No.: 10/096,564

(22) Filed: Mar. 13, 2002

(65) Prior Publication Data

US 2003/0158263 A1 Aug. 21, 2003

(51) Int. Cl.$^7$ .................. A61K 31/135; A61K 9/64
(52) U.S. Cl. ................. 424/456; 424/460; 424/461; 514/653
(58) Field of Search ................. 424/440, 441, 424/442, 464, 446, 499, 465, 451, 456, 405, 420, 433, 463; 514/649, 850

(56) References Cited

U.S. PATENT DOCUMENTS

| | | | | |
|---|---|---|---|---|
| 4,020,159 A | * | 4/1977 | Herrmann | 424/180 |
| 4,708,834 A | * | 11/1987 | Cohen et al. | 264/4.3 |
| 4,797,288 A | * | 1/1989 | Sharma et al. | 424/476 |
| 5,112,602 A | | 5/1992 | Miki et al. | |
| 5,114,929 A | * | 5/1992 | Vartan | 514/29 |
| 5,175,002 A | | 12/1992 | Torosian | |
| 5,409,907 A | | 4/1995 | Blasé et al. | |
| 5,595,758 A | * | 1/1997 | Adudumilli et al. | 424/456 |
| 6,309,677 B1 | | 10/2001 | Gorenbein et al. | |

* cited by examiner

*Primary Examiner*—Thurman K. Page
*Assistant Examiner*—M. P Young
(74) *Attorney, Agent, or Firm*—Knobbe Martens Olson & Bear LLP

(57) ABSTRACT

The present invention relates to a pharmaceutical formulation for oral administration through a soft gelatin capsule drug delivery device, wherein the pharmaceutical formulation has Pseudoephedrine HCl as the active pharmaceutical ingredient. The active pharmaceutical ingredient is embedded into an oily matrix, also the formulation comprises viscosity imparting agents, a surfactant; a suspending agent; and a suspension medium. The viscosity-imparting agents are partially hydrogenated vegetable oil and colloidal silicon dioxide, the surfactant is lecithin, the suspending agent is yellow beeswax, and the suspension medium is soybean oil. In one preferred embodiment, the formulation consists essentially of about 60 mg by weight of Pseudoephedrine HCl, about 15–25 mg by weight of partially hydrogenated vegetable oil, about 10–20 mg by weight of yellow beeswax, about 2–8 mg by weight of lecithin, about 2–8 mg by weight of silicon dioxide; and about 150–250 mg by weight of soybean oil. Also disclosed is a process for preparing the formulation.

8 Claims, No Drawings

ORALLY ADMINISTRABLE PHARMACEUTICAL FORMULATION

BACKGROUND OF THE INVENTION

1. Field of the Invention

This invention in general relates to orally administrable pharmaceutical formulations and in particular to a pharmaceutical formulation prepared into a soft gelatin capsule containing Pseudoephedrine hydrochloride as the active ingredient.

2. Description of the Related Art

Pseudoephedrine hydrochloride is a drug that has serious potential for abuse. This is so because Pseudoephedrine or Ephedrine could be extracted from various drug products containing Pseudoephedrine hydrochloride and can be converted into amphetamines. Amphetamines have potentially lethal stimulant effects on the central nervous system and heart and are among the most frequent drugs of abuse. Accordingly, it is important to minimize such abuse potential.

Pseudoephedrine HCl is a vasoconstrictor, which produces vasoconstriction by stimulating (alpha)-receptors within the mucous of the respiratory tract. Clinically Pseudoephedrine shrinks the swollen mucous membranes, reduces tissue hyperemia, edema and nasal congestion, and increases nasal airway patency. Its use is therefore significant in the relief from nasal congestion.

Pseudoephedrine HCl tablets used for the temporary relief of nasal congestion such as is caused by common cold are commercially available in various strengths. However, soft gelatin formulations containing only Pseudoephedrine HCl as an active ingredient are not commercially available. The following table contains details of commercially available soft gelatin formulations comprising Pseudoephedrine HCl or Pseudoephedrine in combination with antihistamines and/or analgesics.

| Active Ingredient/s (Each Capsule contains) | Brand Name/Manufacturer |
| --- | --- |
| Guaifenesin 200 mg Pseudoephedrine HCl 30 mg Dextromethorphan HBr 10 mg | Robitussin Cold & Cough/ A. H. Robins |
| Pseudoephedrine HCl 30 mg Doxylamine succinate 6.25 mg Dextromethorphan HBr 10 mg Acetaminophen 200 mg | Nyquil/ Proctor & Gamble |
| Pseudoephedrine HCl 30 mg Dextromethorphan HBr 10 mg Acetaminophen 200 mg | Dayquil/ Proctor & Gamble |
| Psueodephedrine HCl 30 mg Doxylamine succinate 6.25 mg Dextromethorphan HBr 10 mg Acetaminophen 325 mg | Alka-Seltzer Plus Night-Time Cold Medicine Bayer |
| Pseudoephedrine HCl 30 mg Chlorpheniramine Maleate 2 mg Dextromethorphan HBr 10 mg Acetaminophen 325 mg | Alka-Seltzer Plus Cold & Cough Medicine Bayer |
| Pseudoephedrine HCl 30 mg Chlorpheniramine Maleate 2 mg Acetaminophen 325 mg | Alka-Seltzer Plus Cold & Cough Medicine Bayer |
| Pseudoephedrine HCl 30 mg Acetaminophen 325 mg | Alka-Seltzer Plus Cold & Sinus Medicine Bayer |
| Pseudoephedrine HCl 30 mg Dextromethorphan HBr 10 mg Acetaminophen 325 mg | Alka-Seltzer Plus Cold & Cough Medicine Bayer |

U.S. Pat. No. 5,409,907 to Blase et. al describes a pharmaceutical suspension comprising a therapeutic amount of pharmaceutically active agent selected from the group consisting of acetaminophen, famotidine, pseudoephedrine hydrochloride, chlorpheniramine maleate, astemizole, dextromethorphan hydrobromide, guaifenesin, diphenhydramine hydrochloride, loperamide hydrochloride, simethicone, antacids, and combinations thereof. However, the suspending system described therein comprises an effective amount of xanthan gum and microcrystalline cellulose.

A composition including soybean oil, yellow beeswax and lecithin has been disclosed in the U.S. Pat. No. 6,309,667 to Horvath et al. This disclosure does not address Pseudoephedrine HCl as an ingredient in combination with the other excipients.

U.S. Pat. No. 5,175,002 is addressed at a suspension formulation comprising soybean oil, lecithin and wax. However the active in this formulation is Amantidine Hydrochloride.

U.S. Pat. No. 5,112,602 to Beurline et al. discloses an oral pharmaceutical liquid suspension comprised of theophylline as the active agent, silicon dioxide, a wetting agent and a hydrocolloid gum.

SUMMARY OF THE INVENTION

It has been found that patient compliance is improved if a soft gelatin capsule is used for drug administration, because of its soft, elastic character which makes it easier to swallow when compared to conventional tablets or hard gelatin capsules. Furthermore, since the dosage form is generally swallowed without chewing, it is unnecessary to flavor or otherwise mask any unpleasant taste of the active pharmaceutical ingredients. Finally, unlike tablets, soft gelatin capsules do not chip or powder. Accordingly, we sought to devise a soft gelatin capsule formulation of Pseudoephedrine HCl because of these and other reasons.

In accordance with one preferred embodiment there is provided an orally administrable pharmaceutical formulation consisting essentially of an active pharmaceutical ingredient embedded into an oily matrix; viscosity imparting agents; surfactant; suspending agent; and suspension medium.

In accordance with one preferred embodiment there are provided soft gelatin capsules of a pharmaceutical formulation consisting essentially of about 60 mg by weight of Pseudoephedrine HCl, about 10–20 mg by weight of yellow beeswax, about 15–25 mg by weight of partially hydrogenated vegetable oil, about 2–8 mg by weight of lecithin, about 2–8 mg by weight of silicon dioxide and about 150–250 mg by weight of soybean oil.

In accordance with another preferred embodiment there are provided methods of making a pharmaceutical formulation comprising the steps of preparing an oily matrix consisting of soybean oil and partially hydrogenated vegetable oil and heat treating the oily blend with beeswax to have the beeswax dissolve or melt into the matrix. The steps of the method further comprise blending lecithin into said oily matrix and mixing the active pharmaceutical ingredient into the matrix. Colloidal silicon dioxide is added to the matrix to form a homogeneous blend and the resultant pharmaceutical complex is enclosed into to a capsule, and preferably contains about 60 mg by weight of Pseudoephedrine HCl, about 10–20 mg by weight of yellow beeswax, about 15–25 mg by weight of partially hydrogenated oil, about 2–8 mg by weight of lecithin, about 2–8 mg by weight of silicon dioxide and about 150–250 mg by weight of soybean oil. In a preferred embodiment, the pharmaceutical complex is enclosed in a soft gelatin capsule/drug delivery device.

One possible advantage of preferred embodiments that the active ingredient (either alone or along with one or more excipients) is coated with wax, making the extraction of Pseudoephedrine and its derivatives more difficult. Yet another advantage of the preferred embodiments is that the drug delivery of the pharmaceutical formulation is achieved by a soft gelatin capsule and this makes it relatively difficult for someone to extract the pharmaceutically active ingredient, unlike the case of a tablet as an OTC drug product. Hence the possibility of abuse of the drug is minimized.

Another possible advantage of preferred embodiments is that preferred formulations include excipients like yellow beeswax and soybean oil, which are natural substances that make the extraction further difficult. This, in conjunction with the soft gelatin encapsulation, makes it relatively a complex multi-step process to extract pseudoephedrine from the oily matrix. Thus the preferred embodiments considerably minimize the potential to abuse the drug product.

DETAILED DESCRIPTION OF THE PREFERRED EMBODIMENT

The present invention relates to pharmaceutical formulations having Pseudoephedrine HCl as the pharmaceutically active ingredient for oral administration in the form of soft gelatin capsules. The formulation also comprises partially hydrogenated vegetable oil, yellow beeswax, colloidal silicon dioxide, soybean oil and lecithin. In preferred embodiments, we have used soybean oil as a suspension medium and yellow beeswax as a suspending agent. Hydrogenated vegetable oil has been used as a viscosity inducing agent and colloidal silicon dioxide is used to achieve uniform dose dispersion in preferred embodiments. In a preferred embodiment, the capsules do not contain any pharmaceutically active materials other than Pseudoephedrine and/or a salt thereof According to preferred embodiments, wax forms part of the fill composition that is inside the gelatin shell. A coating of the pharmaceutically active product in wax and oil mixture is achieved making it difficult to isolate the active from the formulation.

The following examples illustrate preferred embodiments of pharmaceutical compositions comprising Pseudoephedrine HCl as principal ingredient.

EXAMPLES

Example 1

| Ingredients | Composition by weight |
| --- | --- |
| Pseudoephedrine HCl, USP | 60 mg |
| Yellow Beeswax | 10–20 mg |
| Partially Hydrogenated Vegetable Oil | 15–25 mg |
| Lecithin, NF | 2–8 mg |
| Colloidal Silicon Dioxide | 2–8 mg |
| Soybean Oil, USP | 150–250 mg |

Although pseudoephedrine HCl is a preferred form of the active, use of the free base or other salts of pseudoephedrine is also contemplated.

In general, gelatin capsule formulations for soft gelatin capsule comprise raw gelatin, plasticizer, solvent and optional ingredients such as flavors and colorants. Typically the plasticizer includes glycerin or sorbitol. A preferred plasticizer in this case is glycerin. One preferred gelatin formulation for the soft gelatin capsule used in accordance with preferred embodiments includes gelatin in the range of about 40–45% and a plasticizer in the range of about 18–25%. Capsule formulation can also include other suitable additives, which impart specific characteristics such as the look and feel of the capsule.

The following examples illustrate preferred embodiments of several soft-gelatin-shell Pseudoephedrine HCl formulations. These examples illustrate particular embodiments of the invention and are not intended to limit the scope of the invention in any way.

Example 2

| Ingredient | Percentage by weight |
| --- | --- |
| Gelatin | 43.4% |
| Glycerin | 20.0% |
| Water | 36.6% |

Example 3

| Ingredient | Percentage by weight |
| --- | --- |
| Gelatin | 58.5% |
| Glycerin | 31.5% |
| Water | 10.0% |

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the formulations and methods may be formulated or performed in a manner that achieves or optimizes one advantage or group of advantages as taught herein without necessarily achieving other objectives or advantages as may be taught or suggested herein.

Furthermore, the skilled artisan will recognize the interchangeability of various features from different embodiments. Similarly, the various features and steps discussed above, as well as other known equivalents for each such feature or step, can be mixed and matched by one of ordinary skill in this art to perform methods in accordance with principles described herein.

Although the invention has been disclosed in the context of certain embodiments and examples, it will be understood by those skilled in the art that the invention extends beyond the specifically disclosed embodiments to other alternative embodiments and/or uses and obvious modifications and equivalents thereof. Accordingly, the invention is not intended to be limited by the specific disclosures of preferred embodiments herein, but instead by reference to claims attached hereto.

What is claimed is:

1. An orally administrable liquid formulation consisting essentially of Pseudoephedrine hydrochloride and guaifenesin suspended in an oily matrix, said oily matrix consisting essentially of beeswax, soybean oil, lecithin, and colloidal silicon dioxide and/or partially hydrogenated vegetable oil, wherein the formulation is a liquid.

2. The orally administrable formulation of claim 1, wherein the formulation is contained within a soft gelatin capsule.

3. The orally administrable formulation of claim 1, consisting essentially of:
   about 60 mg of Pseudoephedrine HCl,
   about 10–20 mg of yellow beeswax,
   about 15–25 mg of partially hydrogenated vegetable oil,
   about 2–8 mg of lecithin,
   about 2–8 mg of colloidal silicon dioxide; and
   about 150–250 mg of soybean oil.

4. The orally administrable pharmaceutical formulation of claim 3, wherein the formulation is contained within a soft gelatin capsule.

5. The orally administrable pharmaceutical formulation of claim 1, wherein the ratio of beeswax to soybean oil is between about 1:40 and 1:3000.

6. A process for preparing an orally administrable pharmaceutical formulation comprising:
   preparing an oily blend comprising soybean oil and partially hydrogenated vegetable oil;
   heat treating the oily blend with beeswax, wherein the beeswax melts into the oily blend to form an oily liquid matrix;
   blending lecithin into said oily liquid matrix;
   mixing Pseudoephedrine hydrochloride to said matrix to form a suspension of the Pseudoephedrine hydrochloride with the matrix;
   adding colloidal silicon dioxide to the matrix; and
   disposing the resultant pharmaceutical complex into a capsule, wherein said orally administrabJe pharmaceutical is in a liquid form within the capsule.

7. The process of claim 6, wherein the ratio of beeswax to soybean oil is between about 1:7.5 and 1:2500.

8. An orally administrable formulation consisting essentially of Pseudoephedrine hydrochloride suspended in an oily liquid matrix, said oily liquid matrix consisting essentially of beeswax, soybean oil, lecithin, and colloidal silicon dioxide and/or partially hydrogenated vegetable oil, wherein said formulation is made by a method comprising:
   preparing an oily blend comprising soybean oil and partially hydrogenated vegetable oil;
   heat treating the oily blend with beeswax, wherein the beeswax melts into the oily blend to form an oily liquid matrix;
   blending lecithin into said oily liquid matrix;
   mixing Pseudoephedrine hydrochloride to said matrix to form a suspension of the Pseudoephedrine hydrochloride with the matrix;
   adding colloidal silicon dioxide to the matrix; and
   disposing the resultant pharmaceutical complex into a capsule, wherein said orally administrable pharmaceutical is in a liquid form within the capsule.

\* \* \* \* \*